United States Patent
Kim et al.

(10) Patent No.: US 8,541,601 B2
(45) Date of Patent: Sep. 24, 2013

(54) PIPERAZINE DITHIOCTATE AND PHARMACEUTICAL COMPOSITION COMPRISING THE SAME

(75) Inventors: Kyoung Soo Kim, Yongin-si (KR); Young Jun Park, Suwon-si (KR); Hyun-Nam Song, Hwaseong-si (KR); In Suk Lee, Hwaseong-si (KR); Joon Woo Kim, Hwaseong-si (KR)

(73) Assignees: Celltrion Chemical Research Institute, Hwaseong-si (KR); Celltrion Pharm, Inc., Seoul (KR)

( * ) Notice: Subject to any disclaimer, the term of this patent is extended or adjusted under 35 U.S.C. 154(b) by 0 days.

(21) Appl. No.: 13/379,528

(22) PCT Filed: Jun. 18, 2010

(86) PCT No.: PCT/KR2010/003954
§ 371 (c)(1),
(2), (4) Date: Dec. 20, 2011

(87) PCT Pub. No.: WO2010/151008
PCT Pub. Date: Dec. 29, 2010

(65) Prior Publication Data
US 2012/0101107 A1     Apr. 26, 2012

(30) Foreign Application Priority Data
Jun. 24, 2009   (KR) .................. 10-2009-0056337

(51) Int. Cl.
| | |
|---|---|
| C07D 339/04 | (2006.01) |
| A61K 31/385 | (2006.01) |
| A61K 31/497 | (2006.01) |
| C07D 409/06 | (2006.01) |

(52) U.S. Cl.
USPC .......... 549/39; 514/440; 514/252.13; 544/374

(58) Field of Classification Search
None
See application file for complete search history.

(56) References Cited

U.S. PATENT DOCUMENTS

| | | |
|---|---|---|
| 3,562,273 A | 2/1971 | Salat et al. |
| 3,718,664 A | 2/1973 | Salat et al. |
| 5,948,810 A | 9/1999 | Wessel et al. |

(Continued)

FOREIGN PATENT DOCUMENTS

| | | |
|---|---|---|
| DE | 198 18 563 A1 | 10/1999 |
| KR | 10-2006-0011952 A | 2/2006 |

(Continued)

OTHER PUBLICATIONS

Stotzem et al., "Einfluss von alpha-Liponsaeur, Vitamin B oder Gangliosiden auf die Regeneration traumatisch geschaedigter, peripherer Nerven der Ratte," Arzneimittelforschung—Drug Research, 1988, vol. 38, No. 1, pp. 669-671.
European Patent Office, European Search Report issued in corresponding EP Application No. 10792290.8, dated Oct. 26, 2012.

*Primary Examiner* — Timothy Thomas
*Assistant Examiner* — Rayna B Rodriguez
(74) *Attorney, Agent, or Firm* — Sughrue Mion, PLLC

(57) ABSTRACT

The present invention relates to piperazine dithioctate, a novel addition salt of thioctic acid with a base and a pharmaceutical composition comprising the same. The piperazine dithioctate according to the present invention has good thermal and moisture stability and high water-solubility as well as dosage increase lower than other addition salts, thereby being effectively used for preparing a pharmaceutical composition for antioxidation or for preventing or treating diabetic polyneuropathy, etc.

4 Claims, 4 Drawing Sheets

(56) References Cited

U.S. PATENT DOCUMENTS

| | | | |
|---|---|---|---|
| 5,990,152 A | 11/1999 | Hettche et al. | |
| 6,251,935 B1 | 6/2001 | Schoenen et al. | |
| 6,271,254 B1 * | 8/2001 | Ulrich et al. | 514/440 |
| 7,285,664 B2 | 10/2007 | Harnett et al. | |
| 2006/0199847 A1 | 9/2006 | Klatt et al. | |

FOREIGN PATENT DOCUMENTS

| | | |
|---|---|---|
| KR | 10-0903549 B1 | 6/2009 |
| WO | WO 03/011852 A1 | 2/2003 |
| WO | WO 2004/094403 A1 | 11/2004 |

* cited by examiner

PIPERAZINE DITHIOCTATE AND PHARMACEUTICAL COMPOSITION COMPRISING THE SAME

CROSS REFERENCE TO RELATED APPLICATIONS

This application is a National Stage of International Application No. PCT/KR2010/003954 filed Jun. 18, 2010, claiming priority based on Korean Patent Application No. 10-2009-0056337 filed Jun. 24, 2009 the contents of all of which are incorporated herein by reference in their entirety.

TECHNICAL FIELD

The present invention relates to piperazine dithioctate which has good stability and high solubility to be effectively used for preparing a pharmaceutical composition for antioxidation or for preventing or treating diabetic polyneuropathy, etc. and a pharmaceutical composition comprising the same.

BACKGROUND ART

Thioctic acid (alpha-lipoic acid, 6,8-dithioctic acid) has the function of a coenzyme in pyruvate-dehydrogenase complexes, alpha-ketoglutarate-dehydrogenase complexes and amino acid hydrogenase complexes, which is used as an antioxidant and a medicament for preventing or treating diabetic polyneuropathy. Thioctic acid represented by the following formula (II) has pharmacological functions which scavenge free radicals and inhibit lipid peroxidation to reduce oxidative stress, reduce protein glycosylation caused by hyperglycemia, improve glucose disposal rates to normalize neuronal ATP energy production and improve the electrical conductivity of neurons.

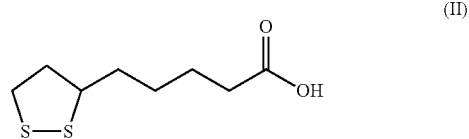 [SMILES: O=C(O)CCCCC1CCSS1]

(II)

Thioctic acid is known as an antioxidant which inhibits oxidative stress or oxidative damage to be effective in diabetic polyneuropathy, liver disease, dementia, Alzheimer's disease, rheumatoid arthritis, increase of lipids in blood vessel, etc., and it is also reported to be effective in treating obesity or obesity-related disorders and migraine (see U.S. Pat. No. 6,251,935).

Thioctic acid, however, shows poor thermal stability and low water-solubility, thereby being difficult to provide pharmaceutical formulations. Thioctic acid has a melting point ranging from 58 to 61° C. in its racemic form and a lower melting point ranging from 47 to 49° C. in its isomer forms. The racemic and isomer forms of thioctic acid are rapidly polymerized to be inactive when they are melted. Also, thioctic acid has a problem of stimulating the esophagus of patients when it is prepared as a liquid formulation to be orally administered. Accordingly, there has been a need to develop a novel crystalline form or base addition salt of thioctic acid which has better stability and higher bioavailability.

As base addition salts of thioctic acid, U.S. Pat. No. 5,990,152 discloses metal salts, and U.S. Pat. Nos. 5,990,152, 3,562,273 and 3,718,664 teach tromethamine salt.

However, the base addition salts of thioctic acid are difficult to be prepared in solid form due to high fat-solubility of thioctic acid. Therefore, the known base addition salts of thioctic acid are mostly amorphous forms, which have low stability against heat and moisture. Among the known base addition salts, only tromethamine thioctate has a crystalline form to have an improved stability against heat and moisture, thereby being clinically used, but it requires a careful clinical use due to enzyme-inhibiting function of tromethamine (see *Structure* 2002, 10: 1063-1072 and *Protein Peptide Lett.* 2008, 15: 212-214). Also, tromethamine thioctate has a problem of significant molecular weight increase due to relatively high molecular weight of tromethamine (121.14 g/mol). Since thioctic acid is used in high dosage ranging from 100 to 600 mg depending on indication, the dosage increases by base addition amounting to 58.7% makes tromethamine thioctate difficult to be developed as a pharmaceutical formulation.

An active ingredient generally should have solubility of 3 mg/ml or higher at pH ranging from 1 to 7 in order to show optimum effect in a pharmaceutical composition considering disintegration rate during in vivo uptake. However, the known tromethamine thioctate is inferior to said solubility at pH 1.2 (stomach condition) and pH 5.2 (intestine condition), thereby showing low bioavailability on oral administration to be difficult to give sufficient effect according to the content of the active ingredient.

Therefore, there has been a need to develop a novel base addition salt having good thermal and moisture stability and high water-solubility, as well as slightly increasing dosage by the addition of a base and employing a pharmaceutically safe organic base. Particularly, in case of a drug for long-term oral administration such as thioctic acid, its stability against heat and moisture is very important since it can be stored and distributed for a long period of time before being taken.

DISCLOSURE

Technical Problem

The present inventors have endeavored to overcome the problems of the known thioctic acid and base addition salts thereof, such as their poor stability and solubility and formulation difficulties due to dosage increase, and found that piperazine dithioctate, a novel addition salt of thioctic acid, has good thermal and moisture stability and high water-solubility as well as a dosage increase lower than other addition salts.

An object of the present invention is, therefore, to provide piperazine dithioctate having superior stability and water-solubility.

Another object of the present invention is to provide a pharmaceutical composition comprising piperazine dithioctate as an active ingredient together with a pharmaceutically acceptable carrier, for antioxidation; for preventing or treating diabetic polyneuropathy, liver disease, obesity, dementia, Alzheimer's disease or rheumatoid arthritis; or for inhibiting increase of lipids in blood vessel.

Technical Solution

One aspect of the present invention relates to piperazine dithioctate of the following formula (I).

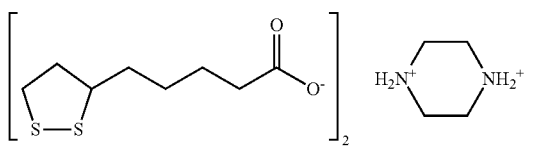

(I)

The thioctate used in the present invention may exist in racemic form or optically active form such as R-(+)-thioctic acid and S-(−)-thioctic acid.

In case of racemic thioctate, a preferred embodiment of the piperazine dithioctate of the present invention is a crystalline form showing an X-ray powder diffraction (XRPD) pattern characterized by peaks having $I/I_o$ values of at least 10% (I is the intensity of each peak; $I_o$ is the intensity of the highest peak) at diffraction angles (2θ) of 13.9±0.2, 16.3±0.2, 17.1±0.2, 17.3±0.2, 18.2±0.2, 18.9±0.2, 20.5±0.2, 22.2±0.2, 22.8±0.2, 24.2±0.2, and 39.3±0.2.

In case of R-(+)-thioctate, a preferred embodiment of the piperazine dithioctate of the present invention is a crystalline form showing an XRPD pattern characterized by peaks having $I/I_o$ values of at least 10% (I is the intensity of each peak; $I_o$ is the intensity of the highest peak) at diffraction angles (2θ) of 14.0±0.2, 19.1±0.2, 20.6±0.2, 22.2±0.2, and 22.7±0.2.

The piperazine dithioctate according to the present invention has overcome the problems of poor stability and solubility that the known thioctic acid and base addition salts thereof have, and contains piperazine, one of the safest organic bases to have pharmaceutically favorable advantages. The piperazine used in the present invention is very safe since it has a $LD_{50}$ (the lethal dose causing death in 50% of rats on oral administration) of 1900 mg/kg (see *Handbook of Pharmaceutical Salts, p* 321 (2008)), and has a relatively low molecular weight of 86.14 g/mol to be favorably used to give a base addition salt. Particularly, the piperazine dithioctate according to the present invention has two thioctic acid molecules bonded to one piperazine molecule, thereby minimizing its dosage increase due to base addition to 20.9% to give a pharmaceutically favorable advantage in thioctic acid formulations with needing a high-dosage.

The piperazine dithioctate of the above formula (I) according to the present invention may be prepared by the reaction of thioctic acid of the following formula (II) with piperazine of the following formula (III) in an organic solvent.

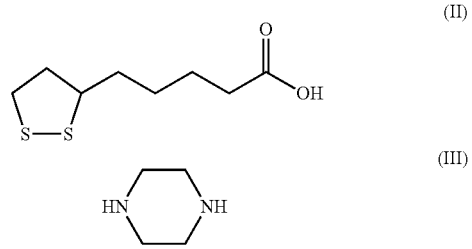

(II)

(III)

The process for preparing the piperazine dithioctate of the present invention is described in more detail below.

The piperazine dithioctate of the present invention is preferably prepared by dissolving thioctic acid and piperazine in an organic solvent, followed by stirring. The thioctic acid and piperazine may be individually dissolved in an organic solvent and mixed, or they may be dissolved together in an organic solvent. In the present invention, piperazine is preferably used in an amount of 0.44 to 0.5 equivalents based on the amount of thioctic acid.

After the reaction of thioctic acid with piperazine in an organic solvent, the process for preparing the piperazine dithioctate according to the present invention may further comprise the step of:

(i) stirring the reaction solution and filtering the solid formed;

(ii) lowering the temperature of the reaction solution, followed by stirring, and filtering the solid formed; or (iii) stirring the reaction solution with adding a precipitating solvent and filtering the solid formed.

The organic solvent used in the present invention may include one or more selected from alcohols such as methanol, ethanol, isopropanol, 1-butanol and hexanol; ethers such as tetrahydrofuran, dioxane and isopropylether; nitriles such as acetonitrile; ketones such as acetone and 2-butanone; esters such as ethyl acetate and isopropyl acetate; and chlorinated hydrocarbons such as dichloromethane, chloroform and 1,2-dichloroethane.

The precipitating solvent used in the present invention may include one or more selected from ethers such as tetrahydrofuran, dioxane and isopropylether; nitriles such as acetonitrile; ketones such as acetone and 2-butanone; hydrocarbons such as n-pentane and n-hexane; aromatic hydrocarbons such as benzene, toluene and xylene; and esters such as ethyl acetate and isopropyl acetate.

The reaction time is preferably 1 to 5 hours, and the reaction temperature is preferably 0 to 40° C.

The process for preparing the piperazine dithioctate of the present invention may further comprise the step of washing and drying the solid obtained after filtering.

Another aspect of the present invention relates to a pharmaceutical composition comprising the inventive piperazine dithioctate together with a pharmaceutically acceptable carrier. In particular, the pharmaceutical composition of the present invention can be used for antioxidation; for preventing or treating diabetic polyneuropathy, liver disease, obesity, dementia, Alzheimer's disease or rheumatoid arthritis; or for inhibiting increase of lipids in blood vessel.

In the pharmaceutical composition of the present invention, the piperazine dithioctate may be used alone or together with other biologically active substances, preferably substances which can show a synergy effect when being used together with piperazine dithioctate.

The pharmaceutical composition according to the present invention can be formulated as tablets, capsules, granules, powders, emulsions, suspensions, syrups, etc. The above various forms of the pharmaceutical composition of the present invention can be prepared in a manner well known in the art using a pharmaceutically acceptable carrier(s) which are usually used for each form. Examples of the pharmaceutically acceptable carriers include excipient, filler, extender, binder, disintegrating agent, lubricant, preservative, antioxidant, isotonic agent, buffer, coating agent, sweetening agent, dissolvent, base, dispersing agent, wetting agent, suspending agent, stabilizer, colorant, flavoring agent, etc.

The pharmaceutical composition of the present invention contains 1 to 90 wt %, preferably 10 to 80 wt % of the inventive piperazine dithioctate depending on the form thereof.

The specific dosage of the present pharmaceutical composition can be varied with species of mammals including a human-being, body weight, gender, age, severity of disease, judgment of doctor, etc. It is preferable that 0.5 to 30 mg of the active ingredient is administered per kg of body weight a day for oral use. The total daily dosage can be administered once or over several times depending on the severity of disease, judgment of doctor, etc.

Advantageous Effects

The piperazine dithioctate according to the present invention has high water-solubility at a wide pH range including stomach and intestine pH conditions to show an enhanced in vivo uptake and bioavailability. Also, the inventive piperazine dithioctate has good thermal and moisture stability to be superior in terms of preparation, storage and distribution, and its dosage increase due to base addition is minimized to 20.9% to give a pharmaceutically favorable advantage in thioctic acid formulations with needing a high-dosage.

Accordingly, the piperazine dithioctate of the present invention can be effectively used for preparing a pharmaceutical composition for antioxidation; for preventing or treating diabetic polyneuropathy, liver disease, obesity, dementia, Alzheimer's disease or rheumatoid arthritis; or for inhibiting increase of lipids in blood vessel.

BEST MODE

The present invention is further illustrated by the following examples, which are not to be construed to limit the scope of the invention.

Example 1

Preparation of Piperazine Dithioctate 10.00 g (48.5 mmol) of thioctic acid was added to 100 ml of acetone and completely dissolved therein, and the reaction solution was cooled to 10 to 15° C. In another reaction vessel, 1.90 g (21.8 mmol) of piperazine was completely dissolved in 100 ml of acetone and then added dropwise to the thioctic acid solution obtained above for 1 hour. The reaction solution was cooled to 0 to 5° C. and stirred for 2 hours. The white crystalline solid formed was filtered, washed with 50 ml of cooled acetone and dried under vacuum at 35° C. for 24 hours to give 10.52 g of the target compound (Yield: 96.7%).

Figure 1:
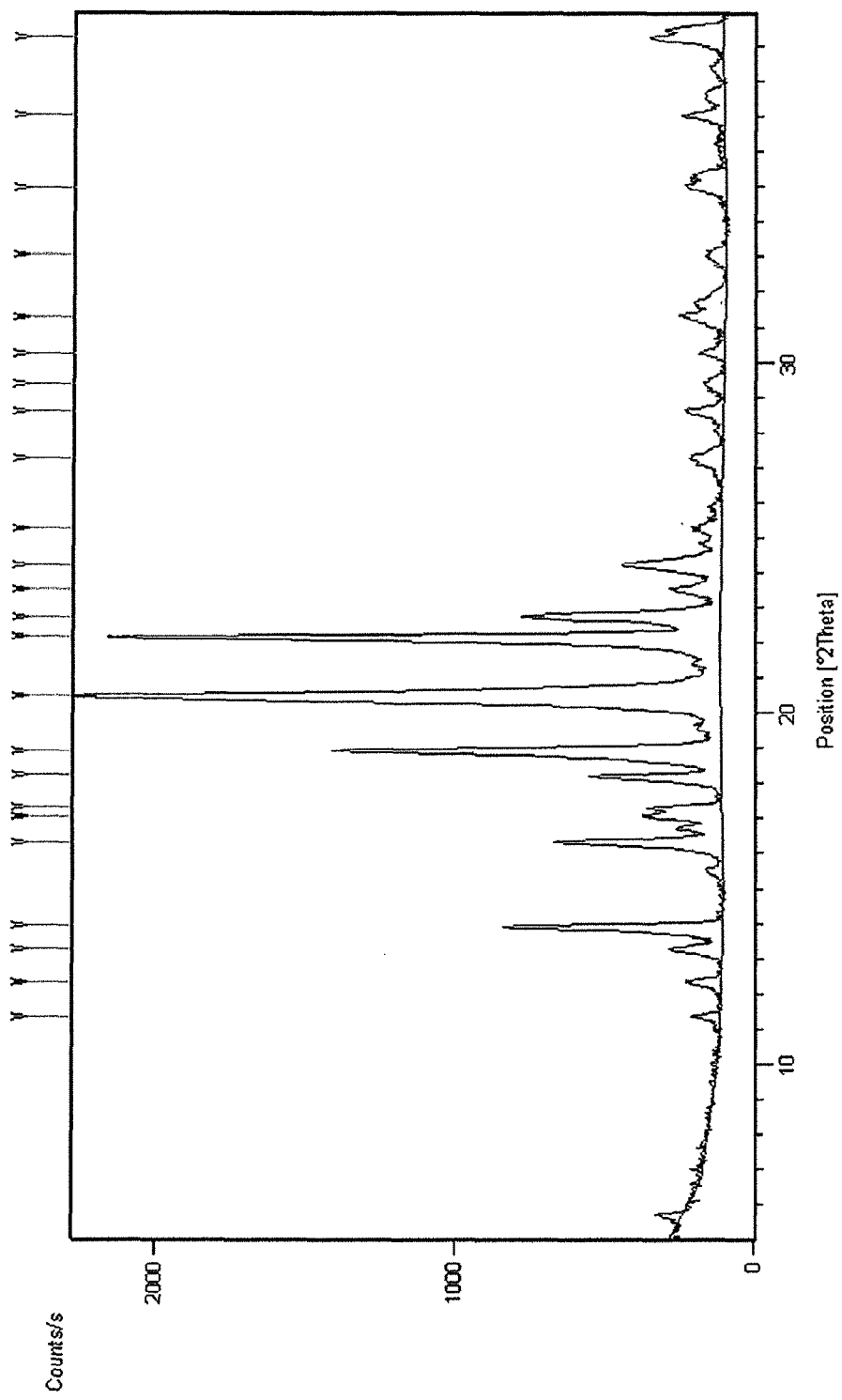
FIG. 1 is an X-ray powder diffraction (XRPD) pattern of the crystalline piperazine dithioctate obtained in Example 1.
Figure 2:
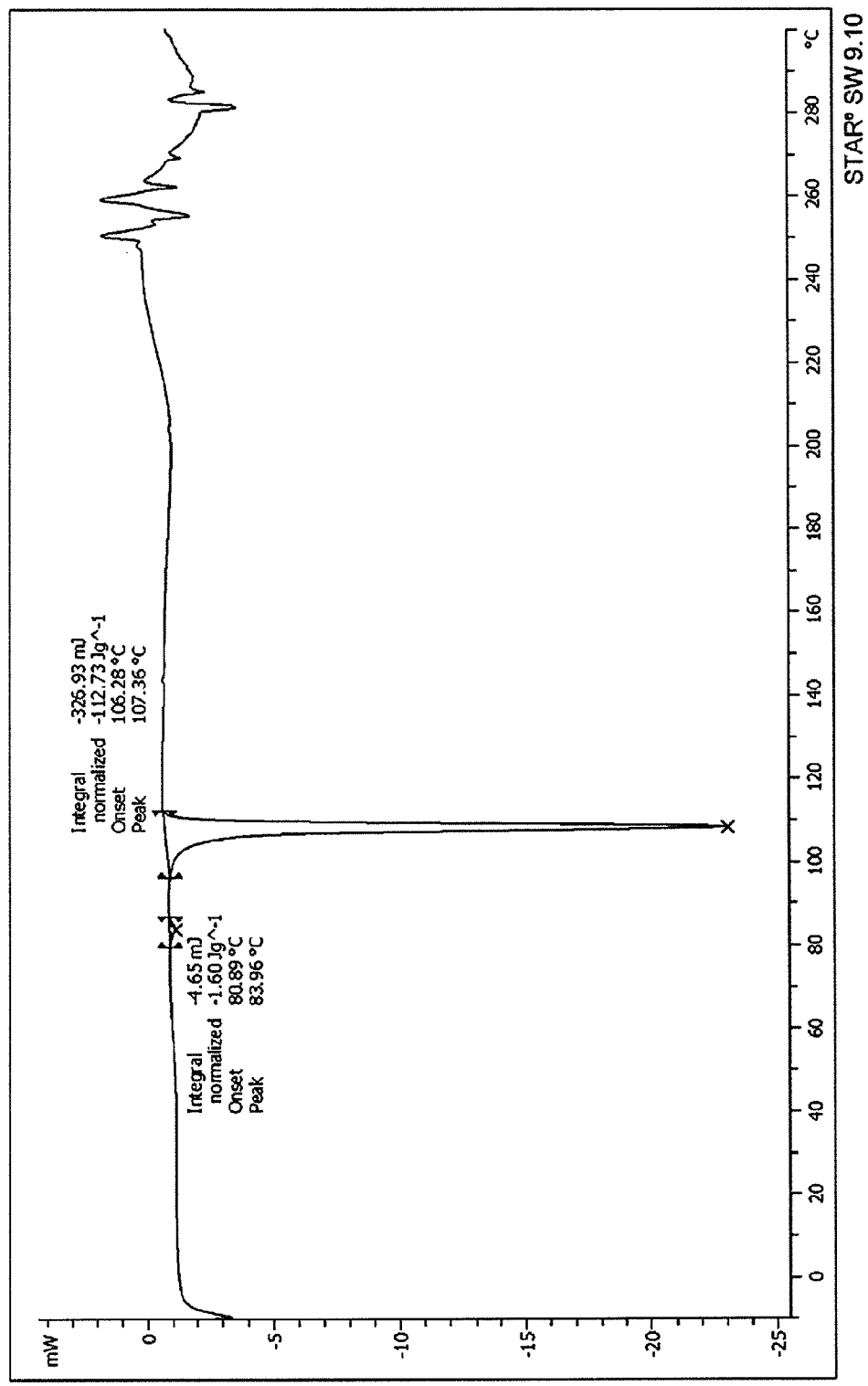
FIG. 2 is a differential scanning calorimeter (DSC) thermogram of the crystalline piperazine dithioctate obtained in Example 1.

The crystalline piperazine dithioctate obtained above was subjected to X-ray powder diffraction (XRPD) and differential scanning calorimeter (DSC) analyses and the results are shown in FIGS. 1 and 2, respectively.

M.P.: 105~106° C.

$^1$H NMR (400 MHz, DMSO-d$_6$): δ=3.57~3.56 (m, 2H), 3.15~3.06 (m, 4H), 2.69 (s, 8H), 2.40~2.35 (m, 2H), 2.10~2.06 (m, 4H), 1.85~1.80 (m, 2H), 1.68~1.59 (m, 2H), 1.55~1.44 (m, 6H), 1.36~1.30 (m, 4H)

Example 2

Preparation of Piperazine Di-R-(+)-thioctate 10.00 g (48.5 mmol) of R-(+)-thioctic acid was added to 100 ml of acetone and completely dissolved therein, and the reaction solution was cooled to 10 to 15° C. In another reaction vessel, 1.90 g (21.8 mmol) of piperazine was completely dissolved in 100 ml of acetone and then added dropwise to the R-(+)-thioctic acid solution obtained above for 1 hour. The reaction solution was cooled to 0 to 5° C. and stirred for 2 hours. The white crystalline solid formed was filtered, washed with 50 ml of cooled acetone and dried under vacuum at 35° C. for 24 hours to give 10.04 g of the target compound (Yield: 92.3%).

Figure 3:
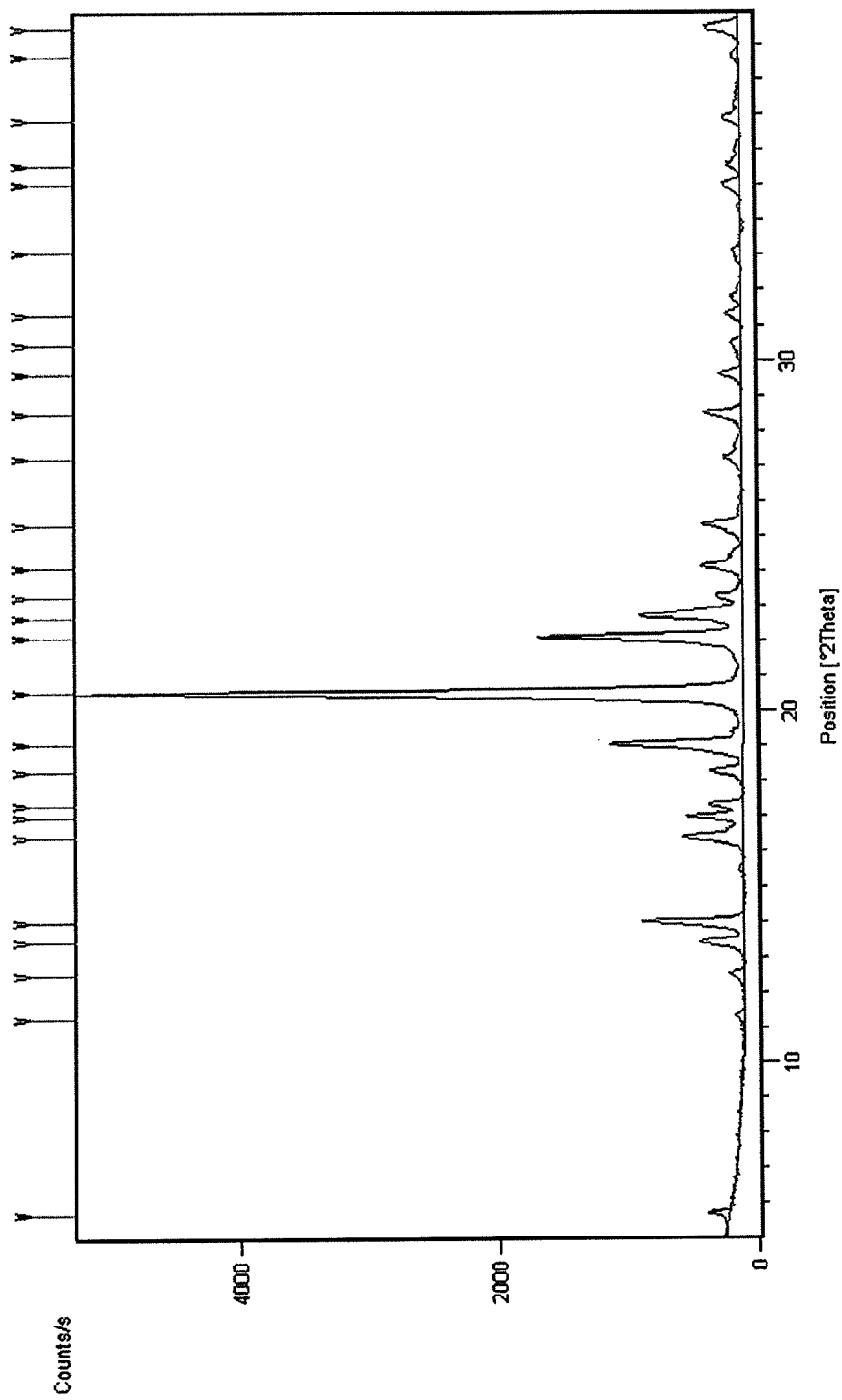
FIG. 3 is an X-ray powder diffraction (XRPD) pattern of the crystalline piperazine di-R-(+)-thioctate obtained in Example 2.
Figure 4:
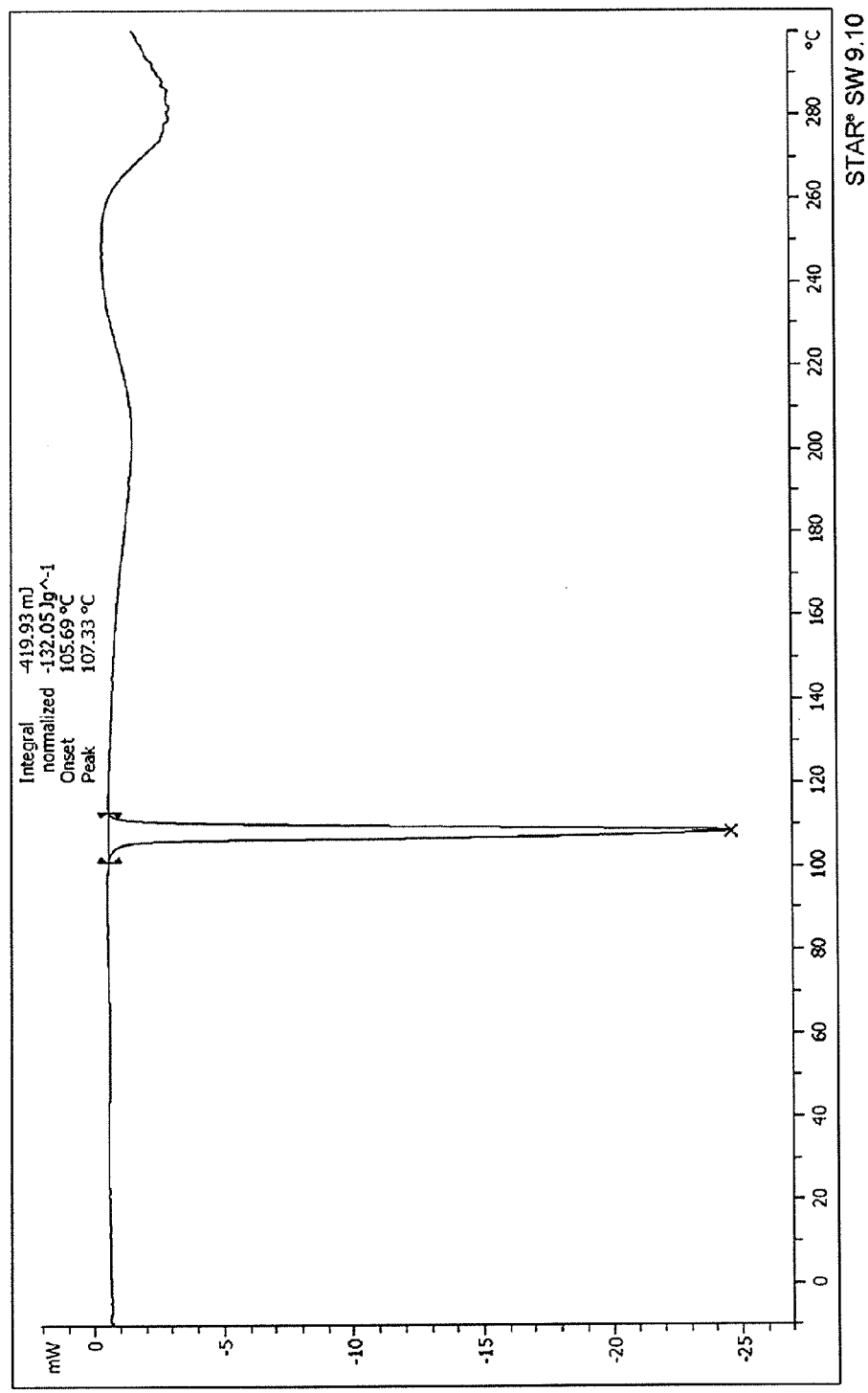
FIG. 4 is a differential scanning calorimeter (DSC) thermogram of the crystalline piperazine di-R-(+)-thioctate obtained in Example 2.

The crystalline piperazine di-R-(+)-thioctate obtained above was subjected to X-ray powder diffraction (XRPD) and differential scanning calorimeter (DSC) analyses and the results are shown in FIGS. 3 and 4, respectively.

M.P.: 103~104° C.

$^1$H NMR (400 MHz, DMSO-d$_6$): δ=3.57~3.56 (m, 2H), 3.15~3.06 (m, 4H), 2.69 (s, 8H), 2.40~2.35 (m, 2H), 2.10~2.06 (m, 4H), 1.85~1.80 (m, 2H), 1.68~1.59 (m, 2H), 1.55~1.44 (m, 6H), 1.36~1.30 (m, 4H)

$[α]_D^{20}$=+73.5~74.5° (c=1.0 in methanol)

Reference Example 1

Preparation of Tromethamine Thioctate 20.00 g (96.9 mmol) of thioctic acid was completely dissolved in 200 ml of ethanol and 11.75 g (96.9 mmol) of tromethamine was added thereto, followed by stirring at 20 to 25° C. for 1 hour. The reaction solution was concentrated, and 100 ml of acetone was added thereto, followed by stirring at 20 to 25° C. for 1 hour. The white crystalline solid formed was filtered and dried under vacuum at 35° C. for 24 hours to give 27.74 g of the target compound (Yield: 87.4%).

$^1$H NMR (400 MHz, DMSO-d$_6$): δ=5.50 (brs, 6H), 3.57~3.54 (m, 1H), 3.28 (s, 6H), 3.15~3.03 (m, 2H), 2.39~2.35 (m, 1H), 2.04~2.00 (m, 2H), 1.86~1.80 (m, 1H), 1.63~1.29 (m, 6H)

Experimental Example 1

X-ray Structure Analysis of Crystalline Piperazine Dithioctate

As shown in FIGS. 1 and 3, the crystalline piperazine dithioctate and the crystalline piperazine di-R-(+)-thioctate obtained in Examples 1 and 2, respectively, have distinctively characteristic peaks in the X-ray powder diffraction (XRPD) patterns. The observed characteristic peaks shown in the XRPD patterns of FIGS. 1 and 3 are listed in Tables 1 and 2, respectively, wherein '2θ' is diffraction angle, 'd' is interplanar spacing, and '$I/I_0$' is relative intensity of the peak.

TABLE 1

| XRPD result of piperazine dithioctate | | |
| --- | --- | --- |
| 2θ | d | $I/I_0$ |
| 11.3355 | 7.80616 | 3.82 |
| 12.3478 | 7.16840 | 5.59 |
| 13.2829 | 6.66580 | 8.34 |
| 13.9230 | 6.36074 | 33.01 |
| 16.3309 | 5.42791 | 26.63 |

TABLE 1-continued

XRPD result of piperazine dithioctate

| 2θ | d | I/I₀ |
|---|---|---|
| 17.0523 | 5.19986 | 12.13 |
| 17.3023 | 5.12529 | 10.72 |
| 18.2115 | 4.87141 | 20.26 |
| 18.9359 | 4.68665 | 60.99 |
| 20.5050 | 4.33144 | 100.00 |
| 22.1630 | 4.01101 | 94.49 |
| 22.7546 | 3.90806 | 31.40 |
| 23.5118 | 3.78387 | 7.70 |
| 24.2192 | 3.67494 | 15.68 |
| 25.2658 | 3.52503 | 4.18 |
| 27.2458 | 3.27319 | 5.10 |
| 28.6022 | 3.12098 | 5.89 |
| 29.3948 | 3.03861 | 3.03 |
| 30.2641 | 2.95328 | 3.72 |
| 31.2762 | 2.85998 | 6.31 |
| 33.0783 | 2.70817 | 2.92 |
| 34.971 | 2.56582 | 5.86 |
| 37.0305 | 2.42771 | 6.68 |
| 39.2636 | 2.29463 | 11.67 |

TABLE 2

XRPD result of piperazine di-R-(+)-thioctate

| 2θ | d | I/I₀ |
|---|---|---|
| 5.6892 | 15.53456 | 3.27 |
| 11.2961 | 7.83335 | 1.1 |
| 12.5019 | 7.08038 | 2.36 |
| 13.4612 | 6.5779 | 6.13 |
| 14.0234 | 6.31541 | 15.7 |
| 16.4425 | 5.39131 | 9.18 |
| 17.0143 | 5.21139 | 8.65 |
| 17.3441 | 5.11303 | 5.33 |
| 18.3264 | 4.84114 | 4.68 |
| 19.1000 | 4.64678 | 19.25 |
| 20.5645 | 4.31904 | 100 |
| 22.1514 | 4.01309 | 31.05 |
| 22.6953 | 3.91812 | 15.86 |
| 23.3229 | 3.8141 | 3.99 |
| 24.1467 | 3.6858 | 6.77 |
| 25.3538 | 3.51299 | 6.06 |
| 27.2567 | 3.27191 | 2.65 |
| 28.506 | 3.1313 | 5.71 |
| 29.6176 | 3.01626 | 3.58 |
| 30.4746 | 2.93336 | 1.51 |
| 31.3347 | 2.85477 | 2.54 |
| 33.1141 | 2.70533 | 1.25 |
| 35.0518 | 2.56009 | 2.84 |
| 35.5721 | 2.52383 | 2.04 |
| 36.8964 | 2.43622 | 2.62 |
| 38.6786 | 2.32798 | 1.03 |
| 39.4902 | 2.28198 | 5.25 |

Experimental Example 2

Moisture and Thermal Stability Test

Since the stability against moisture and heat of an active ingredient in a pharmaceutical composition is an important factor for the production process and long-term storage of the pharmaceutical composition, the stability of the crystalline piperazine dithioctate obtained in Example 1 was measured and compared with those of the known thioctic acid and tromethamine thioctate. Specifically, each compound was stored in a sealed state under an accelerated condition (a temperature of 40° C. and a relative humidity of 75%), and after 0, 3, 7, 14 and 28 days, the remaining rate of the active ingredient was analyzed with a high performance liquid chromatography (HPLC). The results are listed in Table 3.

TABLE 3

| Compound | Initial | 3 days | 7 days | 14 days | 28 days |
|---|---|---|---|---|---|
| Thioctic acid | 100.0 | 99.8 | 99.6 | 98.9 | 97.8 |
| Tromethamine thioctate | 100.0 | 100.0 | 100.0 | 100.0 | 100.0 |
| Piperazine dithioctate | 100.0 | 100.0 | 100.0 | 100.0 | 100.0 |

As shown in Table 3, the crystalline piperazine dithioctate was highly stable even when exposed to an accelerated condition for 28 days, as compared with the known thioctic acid. Such a result suggests that the crystalline piperazine dithioctate of the present invention has good chemical stability to be useful for a medicament for antioxidation or for preventing or treating diabetic polyneuropathy.

Experimental Example 3

Solubility Test at in vivo pH range

Since the water-solubility of an active ingredient in a pharmaceutical composition has effects on the dissolution rate and bioavailability of the pharmaceutical composition, the solubility of the crystalline piperazine dithioctate obtained in Example 1 was measured and compared with those of the known thioctic acid and tromethamine thioctate. Specifically, the solubility measurement was performed at a pH range required for in vivo uptake, that is, at the stomach pH value of 1.2, at the intestine pH value of 5.2 and at the blood pH value of 7.4. Each compound was individually dissolved to saturation, the saturated solutions were analyzed with a high performance liquid chromatography (HPLC), and the dissolved amounts of each compound were measured based on free thioctic acid. The results are listed in Table 4.

TABLE 4

| Compound | Deionized Water (mg/ml) | pH 1.2 (mg/ml) | pH 5.2 (mg/ml) | pH 7.4 (mg/ml) |
|---|---|---|---|---|
| Thioctic acid | 0.90 | 0.78 | 1.62 | 8.24 |
| Tromethamine thioctate | 203.96 | 0.78 | 2.17 | 207.35 |
| Piperazine dithioctate | 25.64 | 9.75 | 19.49 | 35.21 |

As shown in Table 4, the crystalline piperazine dithioctate was more soluble at all pH values, as compared with the known thioctic acid. Also, the crystalline piperazine dithioctate of the present invention had optimum solubility of 3 mg/ml or higher at all pH values, as compared with the known tromethamine thioctate, which suggests that the inventive crystalline piperazine dithioctate can be effectively used in a pharmaceutical composition.

The invention claimed is:

1. A crystalline piperazine dithioctate of formula (I):

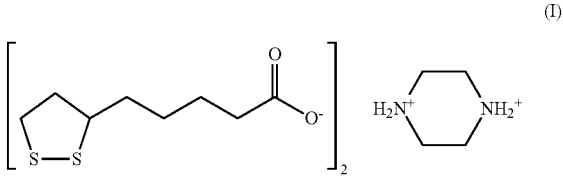

(I)

which shows an X-ray powder diffraction pattern characterized by peaks having I/I₀ values of at least 10% (I is the intensity of each peak; I₀ is the intensity of the highest peak)

at diffraction angles (2θ) of 13.9±0.2, 16.3±0.2, 17.1±0.2, 17.3±0.2, 18.2±0.2, 18.9±0.2, 20.5±0.2, 22.2±0.2, 22.8±0.2, 24.2±0.2, and 39.3±0.2.

2. A crystalline piperazine dithioctate of formula (I):

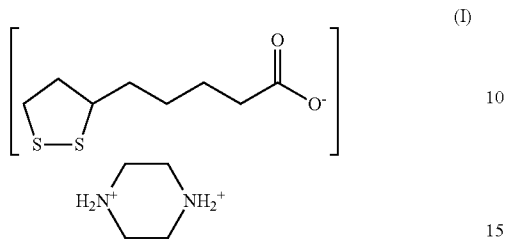

(I)

wherein the thioctate is R-(+)-thioctate or S-(−)-thioctate-; and wherein the crystalline piperazine dithioctate shows an X-ray powder diffraction pattern characterized by peaks having $I/I_o$ values of at least 10% (I is the intensity of each peak; $I_o$ is the intensity of the highest peak) at diffraction angles (2θ) of 14.0±0.2, 19.1±0.2, 20.6±0.2, 22.2±0.2, and 22.7±0.2.

3. A pharmaceutical composition comprising the piperazine dithioctate according to claim 1 together with a pharmaceutically acceptable carrier.

4. A pharmaceutical composition comprising the piperazine dithioctate according to claim 2 together with a pharmaceutically acceptable carrier.

* * * * *